United States Patent [19]

Preston

[11] Patent Number: 5,267,570
[45] Date of Patent: Dec. 7, 1993

[54] METHOD OF DIAGNOSING AND TREATING CHRONIC FATIGUE SYNDROME

[76] Inventor: Myra S. Preston, 1816 Truman Rd., Charlotte, N.C. 28205

[21] Appl. No.: 998,543

[22] Filed: Dec. 30, 1992

[51] Int. Cl.$^5$ .............................................. A61B 5/048
[52] U.S. Cl. .................................... 128/731; 128/732
[58] Field of Search ................................ 128/731–732

[56] References Cited

U.S. PATENT DOCUMENTS 3,621,836 11/1971 Nagatomi ............................. 128/731
4,736,751 4/1988 Gevins et al. .
5,013,739 5/1991 Bihari et al. .
5,055,296 10/1991 Wagle et al. .
5,083,571 1/1992 Prichep ............................... 128/731

FOREIGN PATENT DOCUMENTS 1466708 3/1989 U.S.S.R. ............................. 128/731

OTHER PUBLICATIONS

J. F. Lubar, Chapter 7, in *Biofeedback, Principles and Practice for Clinicians*, (Williams and Wilkins, Baltimore, 1989).
J. F. Lubar, *Biofeedback and Self-Regulation*, 16(3): 201 (1991).
*Handbook of the Clinical EEG*, pp. 11, 67 & 81 (1990).
N. Ostrom, *50 Things You Should Known About The Chronic Fatigue Syndrome Epidemic*, pp. 40–41 (1992).

*Primary Examiner*—Angela D. Sykes
*Attorney, Agent, or Firm*—Timothy R. Kroboth

[57] ABSTRACT

The present invention provides a neurodiagnostic method for chronic fatigue syndrome. Brain waves of a patient are evaluated for slow wave activity. Phase reversal in the delta wave band may be a diagnostic marker. The present invention also provides a biofeedback-based, treatment method for chronic fatigue syndrome. The patient is trained to decrease slow wave wave activity.

22 Claims, 5 Drawing Sheets

METHOD OF DIAGNOSING AND TREATING CHRONIC FATIGUE SYNDROME

BACKGROUND OF THE INVENTION

This invention relates to chronic fatigue syndrome.

Chronic fatigue syndrome has been accepted as a disease only recently and is still subject to considerable uncertainty as to how it may be described. It occurs principally in young adults in the age group of about 22 through 35, but can appear in childhood and through middle age. It is primarily characterized by persistent or relapsing, debilitating fatigue or easy fatigability that may come on suddenly with flu-like symptoms, and that does not resolve with bed rest. Flu-like symptoms may include pharyngitis, anterior or posterior cervical or axillary adenopathy, low-grade fever, myalgia, migratory arthralgia without joint swelling or redness, headache, and difficulty concentrating. Symptoms may also include dysautonomia, mood disturbance, personality change, endocrine system change, unexplained generalized muscle weakness, impairment of sleep, and vision changes. Definitive diagnosis is evasive.

It is thought that the disease initially involves the immune system and thereafter affects the central nervous system. Evidence of virological and bacterial involvement has been reported. There is dispute as to whether it is a psychosomatic illness or organic illness. Most investigations have involved attempted isolation of a causative virus or bacteria from a body fluid or tissue. Brain structure, brain blood flow and brain metabolism of chronic fatigue syndrome patients have been evaluated using PET, SPECT and BEAM scanning procedures, but the results have been unhelpful.

As illustrated by U.S. Pat. No. 4,736,751, brain sites giving raise to brain wave activity and the interrelationships between brain sites, have been studied under stimuli. As exemplified by J. F. Lubar, Chapter 7, in *Biofeedback, Principles and Practice for Clinicians* (Williams and Wilkins, Baltimore, 1989), and *Biofeedback and Self-Regulation*, 16(3): 201 (1991), brain waves of children having attention-deficit/hyperactivity disorder have been evaluated during neuropsychometric testing, and the EEG data analyzed by topographic brain mapping.

Topographic brain mapping permits localized brain areas to be compared for function, and permits the comparison of one brain hemisphere with the other. Brain mapping may use electrode placement according to the International 10-20 Electrode Configuration, that is, the placement of twenty-four electrodes on designated scalp areas.

Neuropsychrometric tests are generally used to evaluate mental information processing including auditory and visual memory processing, and include assembling puzzles, placing pictures in a story-telling sequence, reading out loud, reading silently for comprehension, remembering and repeating back a series of numbers in the given or reverse order, mentally performing mathematical calculations, and converting visual memory into a drawing as a test of short term memory and figure ground perception. However, chronic fatigue syndrome patients have neurological signs that are most often soft, not hard.

As can be understood, considerable effort has been spent on chronic fatigue syndrome but definitive diagnosis remains evasive. Accordingly, there is a need for an improved method for diagnosing chronic fatigue syndrome.

As illustrated by Chapter 7, in *Biofeedback, Principles and Practice for Clinicians*, and by *Biofeedback and Self-Regulation*, biofeedback-based training has been used to change brain waves. The training has been used with, for example, attention-deficit/hyperactivity disorder children and with seizure disorder patients.

Varied treatments including drugs and holistic approaches such as herbal remedies, acupuncture and massage, have been tried for chronic fatigue syndrome. As illustrated by U.S. Pat. No. 5,055,296, one comparatively beneficial treatment is the administration of mammalian liver extract. As exemplified by U.S. Pat. No. No. 5,013,739, an opiate receptor antagonist has also been used. Drugs usually prescribed for symptomatic relief include non-steroidal anti-inflammatory drugs, tricyclic antidepressants, sleep-inducing drugs, tranquilizers, and anti-anxiety drugs. However, generally speaking, symptomatic treatment efforts other than to reduce anxiety, have met with little or no success. As a result, stress management and adjustment counseling are often recommended for chronic fatigue syndrome.

As can be understood, an effective treatment method is lacking for chronic fatigue syndrome. Accordingly, there is a need for an improved method for treating chronic fatigue syndrome.

SUMMARY OF THE INVENTION

It is accordingly an object of the present invention to provide an improved method for diagnosing chronic fatigue syndrome.

It is a further object of the present invention to provide an improved method for treatment of chronic fatigue syndrome.

Additional objects, advantages and novel features of the present invention are set forth in the description that follows, and in part will become apparent to those skilled in the art upon examination of the following description or may be learned by practice of the invention. The objects and advantages of the invention may be realized and attained by means of instrumentalities and combinations particularly pointed out in the appended claims.

To achieve the foregoing objects and in accordance with the purpose of the present invention, as embodied and broadly described herein, there is provided a neurodiagnostic method for chronic fatigue syndrome. In one aspect, an awake and alert patient presenting with symptoms of chronic fatigue syndrome, is evaluated for predominance of slow brain wave activity. In another aspect, a patient presenting with symptoms of chronic fatigue syndrome is subjected to a cognitively challenging, neuropsychometric test or test battery, and evaluated for increased slow brain wave activity.

In a further aspect, the delta brain waves of a patient presenting with symptoms of chronic fatigue syndrome, are evaluated for a phase reversal pattern, with or without cognitive challenge. Cognitive challenge may amplify and elicit phase reversal. Phase reversal in the delta wave band may be a marker definitively diagnostic of chronic fatigue syndrome.

Desirably, brain wave data may be converted into a topographical brain map or other plots or graphs or tables to assist or confirm diagnosis.

Also, in accordance with the present invention, there is provided a biofeedback-based, treatment method for chronic fatigue syndrome. In accordance with this treatment method, suitable biofeedback instrumentation is set to indicate the combination of increased brain wave activity within a selected reward frequency and decreased brain wave activity within a selected inhibit frequency. The brain waves of a chronic fatigue syndrome patient are monitored for achievement of the combination, and achievement is indicated to the patient. Continued achievement by the patient changes the patient's brain wave activity in the desired frequency direction. Beneficially, the selected reward frequency is greater than the selected inhibit frequency and may initially be in the range of approximately 0 to 12 Hz, and the selected inhibit frequency may initially be in the range of approximately 0 to 8 Hz.

BRIEF DESCRIPTION OF THE DRAWING

Reference is now made to the accompanying drawing, which forms a part of the specification of the present invention.

DETAILED DESCRIPTION OF THE INVENTION

As indicated above, the present invention focuses upon the central nervous system of a chronic fatigue syndrome patient, as opposed to the organic body structure. As will become understood, it is believed that symptomatic treatment through medication may have been ineffective because the symptoms of chronic fatigue syndrome are centrally mediated, that is, induced by brain dysfunction, rather than the result of a disease process taking place outside the central nervous system.

Generally speaking, evaluation of abnormal brain function focuses upon four brain wave patterns: beta, alpha, theta and delta. The brain waves of a normal awake person are a mixture of the alpha and beta patterns, with alpha waves generally emanating from the back portion of the brain and beta waves generally emanating from the front portion. The beta rhythm (about 12 to 16 or more Hz) predominates when the individual is awake, alert and active. The alpha rhythm (about 8 to 12 Hz, with larger amplitude) generally increases when the individual closes his eyes and his body is relaxed, and is associated with minimal mental activity. The theta rhythm (about 4 to 8 Hz) increases as a normal individual becomes drowsy and slips closer to sleep. The delta rhythm (about 0 to 4 Hz) appears as the individual begins deep sleep.

DIAGNOSTIC METHOD

As indicated above, the diagnostic method of the present invention is based upon several discoveries. In one aspect, it has been found that an awake and alert, chronic fatigue syndrome patient has a predominance of slow brain wave activity in the 0 to 16 Hz range. By "slow wave activity" is meant for purposes of this invention, delta and theta, or delta, or theta activity. More particularly, delta and theta activity (about 0 to 8 Hz) may be dominant to alpha and beta activity (about 8 to 16 Hz); delta activity may be dominant to theta or alpha or beta activity, or dominant to theta, alpha and beta activity (about 4 to 16 Hz); or theta activity may be dominant to delta or alpha or beta activity, or to delta, alpha and beta activity; and so forth.

In another aspect, it has been found that an awake and alert, chronic fatigue syndrome patient has increased slow brain wave activity when subjected to a cognitively challenging, neuropsychometric test or test battery. In a further aspect, it has been found the delta brain waves of an awake and alert, chronic fatigue syndrome patient include a phase reversal pattern. Moreover, it has been found that phase reversal is universally present in the delta brain waves of chronic fatigue syndrome patients, but lacking in the brain waves of individuals who do not have chronic fatigue syndrome. Thus, a marker has been found that may be definitively diagnostic of chronic fatigue syndrome.

In accordance with the diagnostic method of the present invention, brain function of a patient that presents with symptoms of chronic fatigue syndrome, is evaluated. To this end, a suitable diagnostic instrument is set up to permit the evaluation of brain waves beneficially in the range of about 0 to 16 Hz. Particularly useful are a brain mapping machine and software available under the tradename NeuroSearch-24, from Lexicor Medical Technology, Inc. of Colorado. The software provides fast fourier transform of data, and conversion of data into tables, topographic brain maps, other plots and so forth. Other instruments that permit the evaluation of brain waves in the desired frequency range, and other similar software may be likewise used.

Beneficially, extraneous electrical energy-caused artifact is minimized. To this end, the diagnostic instrument is located well away from 60 Hz noise. Accordingly, fluorescent lighting, which is a primary source of 60 Hz noise, should be avoided. Other sources to be avoided are elevators and microwave appliances.

The patient is positioned to minimize body movement artifact. A sitting position in a comfortable chair, may be beneficially selected. If desired, the head may be immobilized by being secured to the chest by a chest strap attached to a chin strap or by other suitable means. The patient is counseled to control eye blink and other body movement. Additional artifact suppression procedures such as low light levels, may be used.

The scalp of the patient is prepared and electrodes are applied. Advantageously, twenty-four electrodes may be placed on designated scalp areas according to the International 10–20 Electrode Configuration. Of these, twenty are recording electrodes and four are ground electrodes. As will become clear, fewer recording electrodes may be used, but benefit is generally found in using the International 10–20 Electrode configuration or another accepted configuration.

Conveniently, an impedance of about 10 ohms or less is obtained from each electrode. Meticulous preparation of the scalp may result in an impedance of about 2 ohms or less. Relatively lower impedance advantageously provides for relatively increased sensitivity. Uniformity of the impedance is beneficial.

EEG data is then acquired through the wave-sensing, electrode leads. Epochs of data are collected, with one epoch being conveniently equal to about four seconds of data. Preferably, a brain wave scan free of artifact is confirmed at the outset. To this end, brain function may be evaluated with the patient in an eyes closed, relaxing condition, an eyes ahead, relaxing condition, or under both conditions.

Advantageously, for subsequent computer analysis, about twenty or more epochs are acquired until at least about twenty or more "clean" epochs are available. By "clean epochs" is meant epochs of data free of artifact. In any event, after sufficient clean EEG data has been acquired, a brain wave reading free of artifact is again beneficially confirmed. As before, brain function may be evaluated with the patient in an eyes closed, relaxing condition, an eyes ahead, relaxing condition, or under both conditions. Thereafter, the patient is released from the set up. Throughout the collection of EEG data, notation is made of movement artifact such as eye blink artifact, in connection with relevant epochs of data.

The EEG data may be reviewed for artifact by setting a voltage threshold generally in the range of about 1-100 mV, typically at about 50 mV, and screening each epoch. Raw EEG data including artifact, are typically rejected. Clean data are read by the clinician and evaluated for abnormalities.

To provide further information for diagnosis, clean data may be converted through the computer software into a series of topographic brain maps, tables, plots and so forth based upon discrete frequency packets, and in accordance with the present invention, such assembled data may be evaluated. This diagnostic step allows rapid review of a large, monotonous body of raw, EEG data, and computer averaging of a large EEG database allows a gain in statistical power. Computer-generated, color plots based upon discrete frequency packets, for example, 0-4 Hz for delta waves, 4-8 Hz for theta waves, 8-12 Hz for alpha waves and 12-16 Hz for beta waves, facilitate diagnosis.

A preponderance of delta activity is found in most chronic fatigue syndrome patients ill for about three years or more, when these patients are evaluated in the awake, alert state. In such patients, activity in the 0-2 Hz range may be dominant to activity in the 2-4 Hz range, or to theta, alpha or beta activity. Also theta activity may be dominant to alpha or beta activity.

In roughly one-third of chronic fatigue syndrome patients in the early stages of the illness, when evaluated in the awake and alert state, theta activity is found to be dominant to delta or alpha or beta activity, or dominant to delta, alpha and beta activity. Any significant delta or theta activity in the waking state of individuals in age group of about 18 to 45, should raise suspicion of abnormality.

Beneficially, in accordance with a further aspect of my diagnostic method, the patient is cognitively challenged during the EEG. Well known, neuropsychometric tests for evaluating cognitive function may be used. Exemplary neuropsychometric tests include listening to a reading, reading silently for comprehension, remembering and repeating back series of numbers in discrete sets of increasing length in the given or reverse order (digits forwards and backwards), and converting visual memory into a drawing as a test of short term memory and figure ground perception (Bender/Gestalt task, and others). Other such tests may also be used.

I have found that cognitively challenging a chronic fatigue syndrome patient elicits increased slow wave activity. More specifically, delta activity may be increased compared to when the patient is unchallenged (for instance, resting with eyes closed), or compared to a control subject under the same cognitive challenge. Likewise, theta activity may be increased. With respect to a patient having dominant delta activity, in particular in the 0-2 Hz range, in the resting condition, the increased delta activity under challenge may be in the 2 to 4 Hz range. A patient having dominant theta activity in the resting condition, may show increased delta or theta activity, or delta and theta activity, under challenge.

I have further found that the degree of increase appears to be relative to the degree of cognitive difficulty. In other words, a more cognitively difficult task may result in relatively greater increase in slow wave activity than a less cognitively difficult task produces. Exemplary of more cognitively difficult tasks are digits forwards and backwards tests.

In accordance with another aspect of my diagnostic method, I have found that cognitive challenge may amplify and even elicit phase reversal in the delta waves. In some chronic fatigue patients, phase reversal may be found in the delta waves without cognitive challenge. However, I have found that the digits backwards task may be highly definitive in patients that otherwise may not manifest phase reversal. In fact, this cognitive challenge task may be the most helpful, because when the task is used, phase reversal may be found, in my experience, in the most patients. With this task in particular, the harder a patient tries to perform the task, the more phase reversal may be manifested.

As indicated, phase reversal in the delta wave band of an awake, alert, chronic fatigue syndrome patient may be a definitive diagnostic marker. Generally speaking, phase reversal may be observed in brain waves of about 2 Hz or less. By phase reversal is meant that the wave moves through a negative phase. For ease of understanding, exemplary phase reversal patterns are circled in the EEG data of FIG. 1. The phase reversal pattern may be monophasic, diphasic or triphasic. For purposes of illustration, I mention that the phase reversal pattern in waves from lead T4 in FIG. 1 appears to be triphasic.

In a sizable, chronic fatigue syndrome, patient population, phase reversal may be found through any of the twenty wave-sensing electrodes of the International 10-20 Configuration. However, under a difficult cognitive challenge such as digits backwards, phase reversal may be predominantly elicited in waves emanating from the temporal lobes and sensory motor strip. The temporal leads are designated T3, T4, T5 and T6, and the sensory motor strip leads are designated FZ, CZ and PZ, in the International 10-20 Configuration. By comparison, under a digits forwards cognitive challenge, phase reversal patterns may be more globally elicited.

Generally speaking, however, phase reversal is localized, that is, it may not be found in waves emanating from any and all brain regions of a particular patient. Thus, the use of a relatively greater number of channels is generally favored because background or comparative activity is relatively easier to establish.

In chronic fatigue syndrome patients, evaluation of brain waves emanating from the temporal lobes may be sufficient for diagnosis, particularly under digits backwards challenge. However, sensory motor strip brain waves may also beneficially be evaluated. Also particularly informative are brain waves emanating from the frontal lobes, which may be evaluated by leads FP1, FP2, F3, F4 of the International Configuration.

In any event, a global evaluation of brain function is often helpful. For instance, in a normal individual with a developing brain, that is, a normal individual typically less than about eighteen years old, phase reversal may be seen. However, the phase reversal tends to be generalized, not localized in origin, and the pattern is found in a wave frequency typically above 4 Hz. Thus, I generally favor a battery of cognitive challenge tasks and the use of for instance, twenty-four electrodes placed in accordance with the International 10-20 Electrode Configuration.

If desired, the clinician may have clean data from selected electrode sites converted into forms other than the topograph, such as a compressed spectral array, the trend and the power spectrum. These various forms of evaluating brain waves may assist in diagnosis. However, diagnosis may be considered complete when increased slow wave activity is observed under cognitive challenge, or when phase reversal is observed in the delta wave band, in particular in brain waves of about 2 Hz or less. Therefore, if phase reversal is not observed even after cognitive challenge particularly with the digits backward test, the patient should not be considered a chronic fatigue syndrome patient.

In contrast to prior investigation of chronic fatigue syndrome patients, the diagnostic method of the present invention focuses on brain function, once it has been determined that the patient presents with symptoms of chronic fatigue syndrome. There is no need to evaluate organic body structure outside the central nervous system, or even brain structure, brain blood flow or brain metabolism. Furthermore, this neurodiagnostic method beneficially involves cognitively challenging a patient during the acquisition of EEG data.

An important feature of my diagnostic method is that data is collected on the full delta brain wave band, that is about 0 to 4 Hz. In the currently available Lexicor NeuroSearch-24 instrument, this band width may be achieved when the analog highpass filter is in an "off" mode, such that data is collected below 2 Hz. By contrast, if the highpass filter were in the "off" mode in the case of a normal individual, brain waves may cross and an unreadable spectrum may result. However, in a chronic fatigue syndrome patient, brain function is generally slow so as to allow for meaningful evaluation of the full delta wave band. On the other hand, if the highpass filter were in an "on" mode in these patients, generalized slow brain waves would be observable, but not phase reversal below 2 Hz, which might lead a clinician to conclude that the patient is merely depressed.

EXAMPLE OF DIAGNOSTIC METHOD

A 34 year old female presents with symptoms of chronic fatigue syndrome. The patient is prepared for evaluation and a topographic brain map using the Lexicor Neurosearch-24 instrument and software. The instrument is set up to permit the evaluation of brain waves in the range of 0.25 to 16 Hz.

Environmental artifact, in particular 60 Hz noise, is minimized. Electrodes are applied to the scalp using the standard International 10-20 electrode configuration. Impedances are obtained from each electrode at about 3 ohms or less. Standard artifact suppression procedures are used. The patient is positioned in a comfortable chair in a sitting position. Movement artifact is minimized.

EEG data (4 seconds per epoch) is then acquired. First, the patient is evaluated in eyes closed and eyes ahead (open), relaxing conditions, and a brain wave reading free of artifact is established. Delta waves are observed to be dominant to theta, alpha or beta waves. Thereafter, cognitive challenges are presented to the patient as follows: the patient reads silently; the patient listens to a reading; a series of numbers of increasing length is read to the patient and the patient is to repeat back a number series in the given order (digits forwards); similarly, the patient is to repeat back a number series in reverse order (digits backwards), and the patient is to perform the Bender/Gestalt test.

Thereafter, the patient is again evaluated in eyes closed and eyes ahead, relaxing conditions, and a brain wave reading free of artifact is confirmed. Notation is made of movement artifact such as eye blink artifact, in connection with relevant epochs of data.

Following the acquisition of data, the patient is released from the set up. Raw EEG data is evaluated for artifact including eye blink artifact. Data including artifact is rejected. All clean epochs of data (74 epochs) are read by the clinician and evaluated for abnormalities, in particular for phase reversal patterns.

Figure 1:
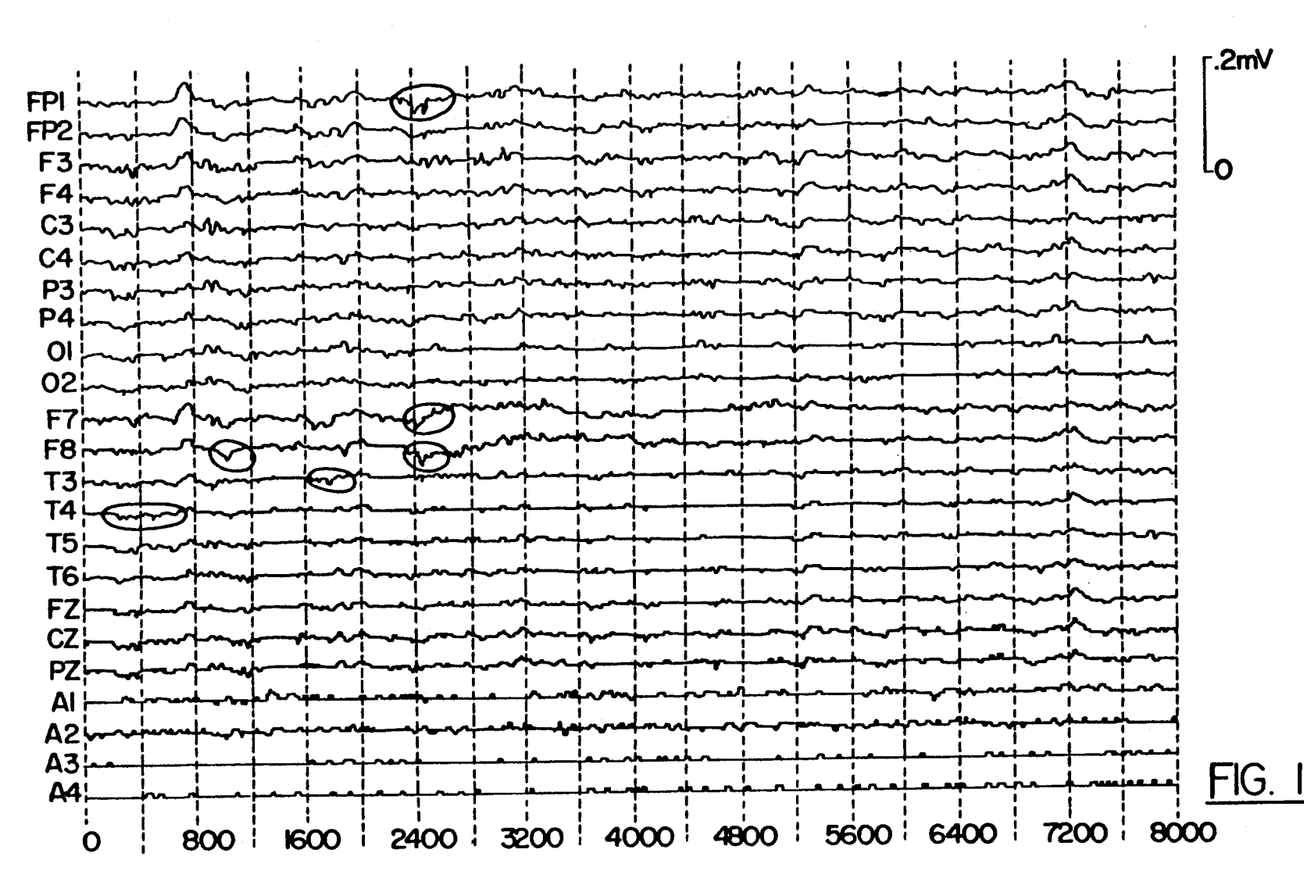
FIGS. 1 and 2 show raw EEG data containing phase reversal patterns.
Figure 2:
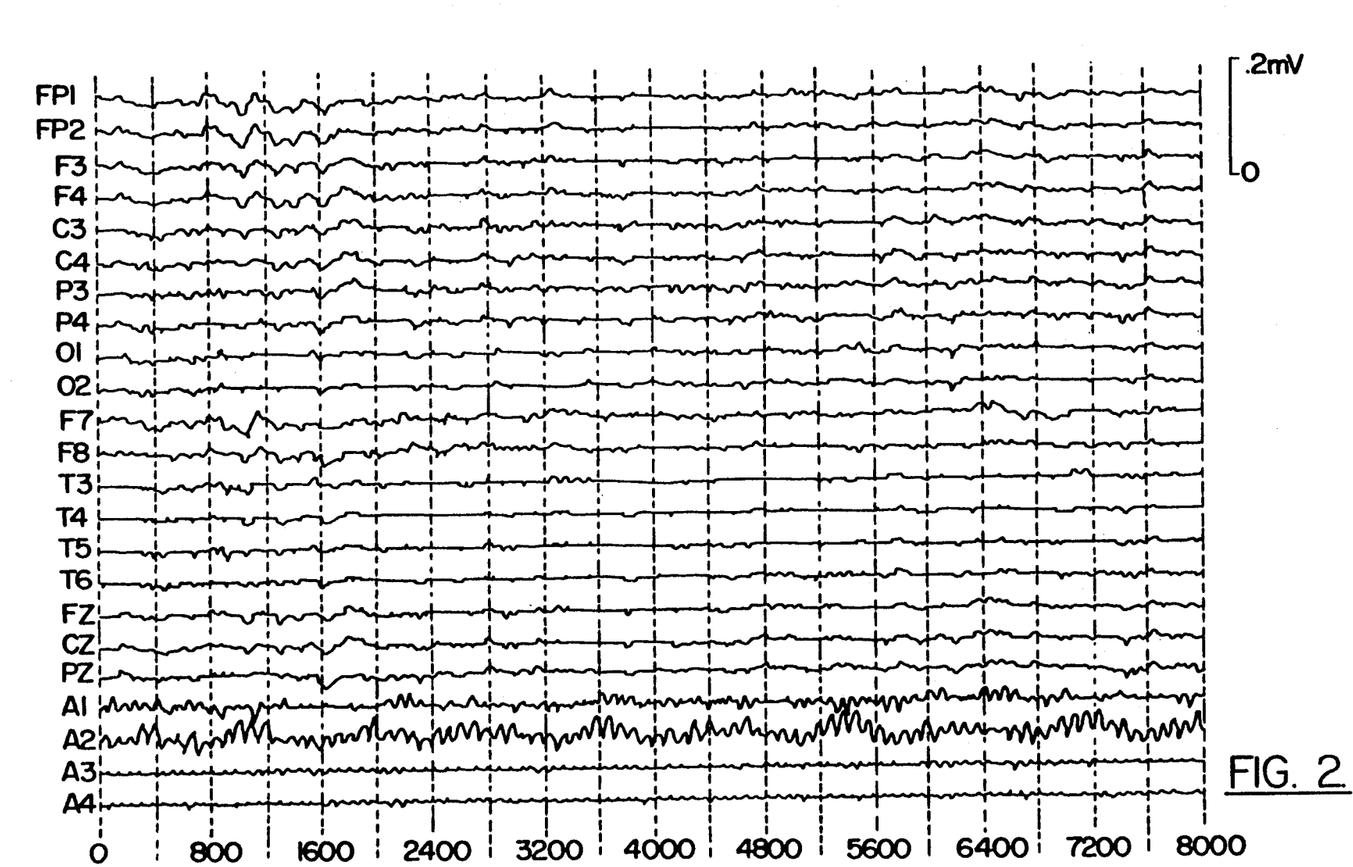

FIG. 1 shows data for epochs 1-2 (resting with eyes closed). FIG. 2 shows data for epochs 54-55 (digits backwards challenge). The data of FIG. 1 show phase reversal, in the unchallenged patient, in delta brain waves emanating from leads FP1, F7, F8, T3, T4 and T5. Brain waves from lead T4 appear to show a triphasic wave pattern. The data of FIG. 2 indicate that the digits backwards task has amplified and elicited phase reversal in the delta brain waves, in particular in delta waves emanating from leads T3, T4, FZ, CZ and PZ. The patient is definitively diagnosed as a chronic fatigue syndrome patient.

Clean epochs of data (resting, eyes closed condition; epochs 1-15, 4 epochs rejected) are converted by the software into Table 1, which shows the relative proportions of activity within indicated brain wave bands. Likewise, clean epochs of data (digits backwards challenge; epochs 47-61, 1 epoch rejected) are converted into Table 2. Tables 1 and 2 (column headings in Hz) confirm the dominance of delta wave activity, reveal the dominance of 0.25 to 2 Hz activity in particular, and show that theta activity is dominant to alpha or beta activity. Moreover, comparison of the Tables shows an increase in delta wave activity under digits backwards challenge, in particular an increase in activity in the 2 to 4 Hz range.

Figure 3:
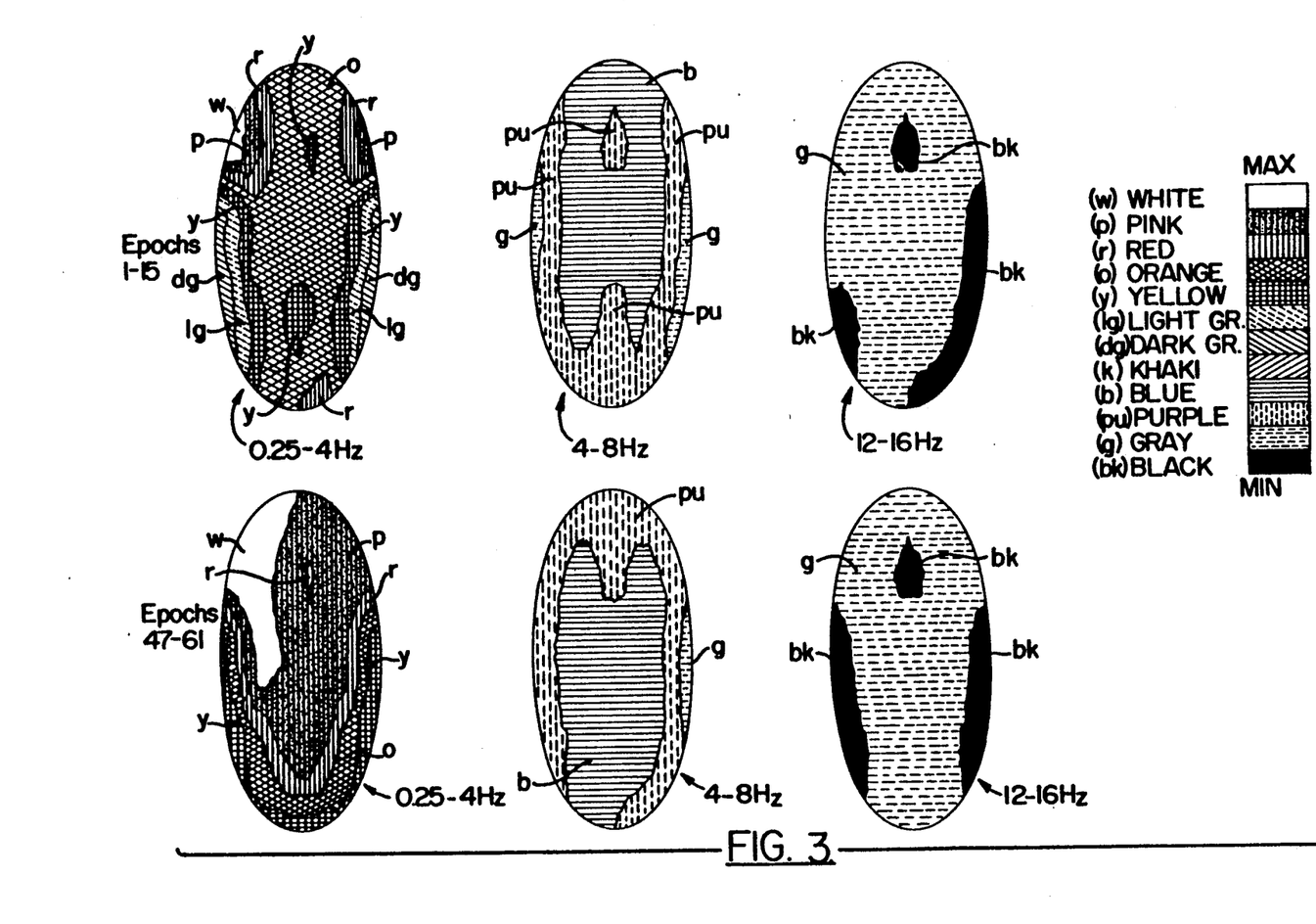
FIG. 3 consists of topographic brain maps.

The data of Tables 1 and 2 are converted by the software into the topographic brain maps of FIG. 3. Each oval topograph depicts a view of the head from above. The forehead is at the top, and the left and right ears are at the left and right sides respectively. Each oval shows density of the indicated brain wave band relative to the other bands, for different brain areas. A scale representing low to high density is displayed as a vertical bar to the right of the ovals.

The topographic brain maps show the dominance of delta wave activity, and that theta activity is dominant to beta activity. Comparison of the brain maps for the resting condition with those for the digits backwards condition shows an increase in delta wave activity under digits backwards challenge.

TREATMENT METHOD

As indicated above, the treatment method of the present invention is based upon several discoveries. In one aspect, it has been found that inhibiting delta wave activity is advantageous for a certain type of chronic fatigue syndrome patient. In this respect, it has been

TABLE 1

| MEAN: | PERCENT POWER | | | | | | TOTAL |
|---|---|---|---|---|---|---|---|
| | 0-2 | 2-4 | 0-4 | 4-8 | 8-12 | 12-16 | (uV2) |
| F7 | 27.2% | 11.5% | 38.7% | 8.9% | 6.5% | 7.3% | 32.0 |
| F8 | 25.9% | 13.8% | 39.7% | 10.1% | 5.6% | 4.9% | 26.5 |
| T5 | 22.6% | 14.8% | 37.4% | 12.2% | 7.1% | 5.9% | 11.4 |
| FP1 | 24.9% | 12.0% | 36.9% | 11.5% | 6.9% | 7.7% | 30.2 |
| F3 | 21.7% | 15.1% | 36.8% | 12.2% | 6.6% | 7.7% | 27.6 |
| C3 | 21.3% | 15.2% | 36.5% | 11.1% | 9.0% | 7.0% | 22.6 |
| P3 | 21.6% | 14.7% | 36.4% | 11.5% | 9.0% | 6.9% | 19.2 |
| O1 | 19.2% | 13.2% | 32.4% | 15.9% | 10.1% | 9.2% | 12.4 |
| FZ | 24.0% | 15.4% | 39.4% | 10.8% | 6.1% | 4.2% | 15.5 |
| CZ | 22.7% | 15.6% | 38.3% | 11.1% | 7.0% | 5.2% | 21.1 |
| PZ | 22.2% | 15.5% | 37.7% | 11.9% | 7.4% | 5.3% | 16.7 |
| FP2 | 25.3% | 13.9% | 39.3% | 11.0% | 5.2% | 5.3% | 24.7 |
| F4 | 23.5% | 15.8% | 39.2% | 11.6% | 5.4% | 4.6% | 25.2 |
| C4 | 22.1% | 15.8% | 37.9% | 11.5% | 7.0% | 5.7% | 24.8 |
| P4 | 24.1% | 13.7% | 37.7% | 10.8% | 7.7% | 5.9% | 20.9 |
| O2 | 29.0% | 10.3% | 39.3% | 10.2% | 5.7% | 5.4% | 18.1 |
| F8 | 25.9% | 13.8% | 39.7% | 10.1% | 5.6% | 4.9% | 26.5 |
| T4 | 27.0% | 14.0% | 41.1% | 9.7% | 4.5% | 3.6% | 10.2 |
| T6 | 24.6% | 13.6% | 38.2% | 10.5% | 6.8% | 6.2% | 10.2 |

TABLE 2

| MEAN: | PERCENT POWER | | | | | | TOTAL |
|---|---|---|---|---|---|---|---|
| | 0-2 | 2-4 | 0-4 | 4-8 | 8-12 | 12-16 | (uV2) |
| F7 | 25.0% | 14.9% | 39.9% | 8.1% | 5.7% | 6.4% | 30.4 |
| F8 | 23.9% | 16.4% | 40.3% | 10.0% | 4.9% | 4.6% | 26.1 |
| T5 | 20.0% | 19.3% | 39.3% | 11.4% | 5.9% | 4.0% | 12.1 |
| FP1 | 23.5% | 16.0% | 39.5% | 9.3% | 5.8% | 5.9% | 32.3 |
| F3 | 21.6% | 18.8% | 40.4% | 10.3% | 4.5% | 4.4% | 33.3 |
| C3 | 20.4% | 19.2% | 39.7% | 10.4% | 6.3% | 4.0% | 32.5 |
| P3 | 18.7% | 19.6% | 38.3% | 12.6% | 6.5% | 4.3% | 28.2 |
| O1 | 16.8% | 15.9% | 32.7% | 16.4% | 10.1% | 8.0% | 14.2 |
| FZ | 23.4% | 18.1% | 41.6% | 10.3% | 3.5% | 3.1% | 22.0 |
| CZ | 19.8% | 21.2% | 41.0% | 10.5% | 4.2% | 3.4% | 29.4 |
| PZ | 20.7% | 19.3% | 40.0% | 11.4% | 5.2% | 3.4% | 27.7 |
| FP2 | 22.7% | 16.5% | 39.2% | 11.0% | 5.5% | 5.0% | 26.6 |
| F4 | 21.6% | 19.1% | 40.7% | 10.8% | 4.4% | 3.5% | 27.4 |
| C4 | 19.3% | 20.4% | 39.7% | 11.1% | 5.7% | 3.8% | 28.6 |
| P4 | 19.2% | 19.8% | 39.0% | 11.4% | 6.5% | 4.1% | 23.7 |
| O2 | 18.1% | 17.6% | 35.8% | 13.6% | 8.0% | 6.9% | 14.0 |
| F8 | 23.9% | 16.4% | 40.3% | 10.0% | 4.9% | 4.6% | 26.1 |
| T4 | 21.0% | 20.2% | 41.1% | 9.2% | 5.2% | 3.3% | 11.1 |
| T6 | 20.0% | 18.0% | 38.0% | 11.4% | 7.7% | 4.9% | 13.0 | found that it may be beneficial to inhibit activity in the lower portion of the delta wave band, that is, about 0-2 Hz, and to increase activity in the upper portion of the delta wave band, that is, about 2-4 Hz, or in the theta wave band, or first in the upper portion of the delta wave band and then in the theta wave band. In a further aspect, it has been found that it may be beneficial to initially inhibit activity in the theta wave band, and increase activity in the alpha wave band, in another type of chronic fatigue syndrome patient. Moreover, it has been found that phase reversal, typically found in the 0-2 Hz frequency range, may be reduced by changing wave activity in the desired frequency direction.

Prior to brain wave training, it is typically advantageous to cognitively prepare the patient by explaining the rationale and goals of training. An eventual goal such as physiological self-regulation, may be mentioned. Moreover, it may be beneficial to pre-train the patient in the use of biofeedback using a modality such as EMG feedback or electrodermal or thermal feedback. Increased patient attention, understanding, confidence and compliance, and reduced anxiety may result.

At the outset, it is generally helpful to evaluate the brain waves of the patient to determine the brain areas where EEG dysfunction in the form of substantial delta or theta activity, may be first found. Based upon this information, a learning paradigm that challenges the patient but provides for success, may be developed. To this end, training parameters are planned, and it may be beneficial to use shaping, that is, target the areas of EEG dysfunction and set up a hierarchy for EEG activity change that initiates change in areas of least dysfunction and progresses to areas of greatest dysfunction. Although the precise learning paradigm to be used will be patient specific, there is, as indicated, commonality.

Beneficially, simultaneous satisfaction of two conditions may be required for reward during training: 1) increased brain wave activity within a specific frequency range (reward frequency); and 2) inhibition of brain wave activity within a specific frequency range (inhibit frequency). Also, inhibition of EMG (muscle artifact) below a chosen microvolt level, typically less than about 2.0 microvolts, may typically be required.

Suitable biofeedback instrumentation is appropriately set by the clinician so that in order to receive a reward, the patient must exert voluntary control over her brain wave activity in a desired frequency direction. More precisely, selected reward and inhibit frequencies, and a suitable reward modality are set to shape the EEG changes in the desired direction.

Feedback is provided through the reward modality. The reward modality informs the patient as to whether, and how frequently, the patient is meeting the conditions for reward, at a given moment. The reward modality may be in the form of analog or binary, auditory or visual signal, or auditory and visual signals, or some other acceptable signal. A typical auditory reward is a discontinuous beeping tone. A visual screen may be used to provide visual reward. In this way, the patient may be rewarded for, and at the same time informed of, increased EEG activity in the reward frequency and inhibition of EEG activity in the inhibit frequency.

Particularly useful biofeedback instrumentation is the A620 EEG Neurofeedback System available from Autogenics Systems of Wood Dale, Ill. This single channel EEG instrument provides for the recording, analysis, and feedback of bipolar EEG activity between two selected sites on a patient's scalp. Feedback is immediate and meaningful. The EEG band passes for the reward and inhibit frequencies are user selectable. The instrument includes a power spectrum display screen, which permits the clinician to observe raw EEG data, the reward frequency, the inhibit frequency, and the number of rewards occurring based on the training parameters set by the clinician.

Other real-time, biofeedback instrumentation that allows the clinician to set training parameters for changing the EEG in the desired frequency direction, may be used. Such instrumentation may provide a channel for each scalp site; however, bipolar recording may be advantageous because common mode artifact may be minimized.

Beneficially, extraneous electrical energy-caused artifact is minimized. To this end, the biofeedback instrumentation is located well away from 60 Hz noise. Accordingly, fluorescent lighting and other sources of 60 Hz noise such as elevators and microwave appliances, should be avoided.

The patient is positioned to minimize body movement artifact. A sitting position in a comfortable chair, may be beneficially selected. The patient is counseled to control eye blink and other body movement. Additional artifact suppression procedures such as low light levels, may be used.

The scalp of the patient is prepared and electrodes are applied. Conveniently, an impedance of about 10 ohms or less is obtained from each electrode. Meticulous preparation of the scalp may result in an impedance of about 2 ohms or less. Relatively lower impedance advantageously provides for relatively increased sensitivity. Uniformity of the impedance is beneficial.

Conveniently, two wave-sensing electrodes may be placed on selected scalp areas according to the International 10-20 Electrode Configuration, and a third electrode applied as a ground. More wave-sensing electrodes may be used, and electrodes may be placed according to another accepted configuration.

Typically, electrodes may initially be applied to the sensory motor strip sites, which are designated FZ, CZ and PZ in the International 10-20 Configuration. When two electrodes are used, one active electrode may be placed at the CZ position, and the other active electrode may be placed at the PZ or FZ position. The sensory motor strip sites advantageously permit simultaneous training of both brain hemispheres and global change to be effected. An ear clip may be applied to serve as the ground.

Other sites may be chosen for the initial training. Selection may be based upon initiating change in areas of least dysfunction to assist patient achievement at the outset of training. After training criteria are met at the initial sites, the clinician may beneficially follow a shaping routine in which sites on one hemisphere are chosen for training, and thereafter the corresponding sites on the other hemisphere are chosen for balanced effect, and so forth, until finally areas of greatest dysfunction have been trained. The sites will vary from patient to patient, and may vary during a session. Suitable training criteria may be for the patient to achieve reward for about thirty percent of a fifteen minute period, while performing a cognitive task.

Often, it may be beneficial to train initially at the sensory motor strip sites and then train at the temporal lobe sites. When training is applied to the sensory motor strip sites first and thereafter to selected hemisphere sites, global training followed by localized training, is advantageously provided.

The patient is instructed in the reward system to be used during training. The training is relatively straightforward. The clinician may sit beside the patient and verbally coach the patient to achieve the reward. The patient may be instructed, for example, to focus her eyes on the screen, to relax, to clear her mind, to focus her attention on the top of her head, and to try to have just one thought until a reward is achieved.

During the training session, EEG data is acquired through the wave-sensing, electrode leads. The instrumentation monitors the EEG data to determine whether the conditions for reward are being achieved, and rewards the patient accordingly. The patient is encouraged to increase the frequency of reward so as to meet training criteria. A typically training session may last for about 40 to 60 minutes; however, the length of the training session will depend upon the patient's physical and intellectual stamina. As many as forty to sixty or more training sessions may be in order.

Generally speaking, I divide chronic fatigue syndrome patients into two groups. One such group of patients reports that disease onset was more with flu-like symptoms than with cognitive dysfunction. The other group of patients reports that the disease onset was more in the context of cognitive dysfunction than with flu-like symptoms.

In accordance with one aspect of the treatment method of the present invention, a patient in the second group of patients is beneficially trained to inhibit activity in the lower portion of the delta wave band, that is, in the approximately 0-2 Hz range. In combination in the upper portion of the delta wave band, that is, in the 2-4 Hz range, or to increase activity in the theta wave band.

To this end, the reward frequency may be set to about 2-4 Hz, and the inhibit frequency may be set to about 0-2 Hz so as to target an approximately one to two Hz increase within the delta wave band for reward. Thus, the initial training may be to increase EEG activity in the upper portion of the delta wave band while simultaneously inhibiting EEG activity in the lower portion of the delta wave band.

Alternatively, the reward frequency may be set to, for example, about 4-5 Hz, and the inhibit frequency may be set to about 0-2 Hz so as to target, for instance, an approximately one to four Hz increase for reward. As the patient meets training criteria with these frequency settings, the inhibit frequency may be broadened to include more and even the entirety of the delta band. This more difficult training protocol may be initially used on a patient within the second patient group who lacks dominant delta wave activity or has dominant theta wave activity. Such patients are generally able at the outset, to increase activity in the theta wave band while inhibiting activity in the delta wave band.

If during training, no or insufficient reward is achieved by the patient within several minutes, the clinician may wish to check the raw EEG signal in the context of the selected reward and inhibit frequencies, and if appropriate, to reset these training parameters. Since each patient's EEG and progress are unique, the initial training session may involve routine experimentation to establish the proper training parameters. For example, it might be appropriate when training a patient to decrease delta wave activity, to broaden the inhibit frequency to include more of the delta wave band, or to broaden the reward frequency to include more and possibly all of the 4 to 8 Hz band.

In accordance with another aspect of the treatment method of the present invention, a patient in the first group of patients may be beneficially trained, at the outset, using sets for increased EEG activity in the alpha wave band and inhibited EEG activity in the theta wave band. This training may be achieved by targeting an approximately one to four Hz increase for reward. Thus, for instance, the reward frequency may be about 8–12 Hz, and the inhibit frequency may be about 4–8 Hz. By contrast, the illness of such a patient worsens when training protocol for increased beta activity (12 to 16 Hz) and inhibition of theta activity (4 to 8 Hz), are used.

Sets for increased alpha activity and inhibition of theta activity may be advantageously used for a patient in the second group of patients, after training criteria have been met for increased theta activity and inhibited delta activity. In such patients, it appears to be helpful to particularly target a reduction in the 0–2 Hz portion of the delta wave band. By this treatment approach, sleep onset insomnia, a common symptom, may be dramatically corrected.

After training criteria have been met with regard to the sets for increased alpha wave activity and inhibition of theta wave activity, the patient may be advantageously trained using sets for increased EEG activity in the beta wave band and inhibited EEG activity in the theta wave band. This training may be achieved by targeting an approximately one to four Hz increase for reward. Thus, for example, the reward frequency may be about 12–16 Hz, and the inhibit frequency may be about 4–8 Hz.

Generally speaking, it is advantageous to train at the initially selected sites by use of the foregoing protocol. Thereafter, as explained, other appropriate sites within the shaping paradigm may be selected and the foregoing protocol repeated.

In terms of relative distribution of wave activity within the 0 to 16 Hz range, use of the foregoing treatment protocol including training for increase in alpha wave activity, produces particularly noticeable reduction in activity in the 0–2 Hz portion of the delta wave band, and increase in theta band activity. Moreover, training for increase in beta wave activity, further significantly reduces EEG activity in the 0–2 Hz range, and increases activity in the theta wave band. Also, phase reversal is diminished but does remain.

Also, by the treatment method of the present invention, the amplitude of the slow wave activity is decreased. In combination therewith, sleep spindles are increased. These spindles are associated with the onset of sleep.

Typically, the first symptom to resolve during training, is sleep disturbance. Symptom abatement may then follow this order: decreased irritability and improved mood stability, decreased headache, improved concentration, and decreased nausea and increased appetite. Body pain changes last, if at all.

In contrast to prior treatment of chronic fatigue syndrome patients, the treatment method of the present invention focuses on brain function. Organic body structure is not directly treated apart from the central nervous system.

EXAMPLE OF TREATMENT METHOD

A 25 year old female presents with symptoms of cognitive difficulty, sleep onset insomnia, anxiety, high irritability, and intense burning and aching in the lower legs and feet. The cognitive difficulties are described as primarily a loss of short term memory and the ability to comprehend conversation with others. She reports great difficulty extracting information from the environment, being slow or uncertain in decision-making, feeling "in a fog", and being unable to concentrate long enough even to read short articles for pleasure.

The patient is prepared for treatment using the A620 EEG Neurofeedback System available from Autogenics Systems of Wood Dale, Ill. Two electrodes are applied to the scalp, and an ear clip is applied to the left ear to serves as the ground. Impedances of less than 10 ohms are obtained from each electrode.

Extraneous electrical energy-caused artifact, in particular 60 Hz noise, is minimized. Standard artifact suppression procedures are used. The patient is positioned in a comfortable chair in a sitting position. Movement artifact is minimized.

The training protocol used is specific to the patient's EEG dysfunction, physical and intellectual stamina, and progress. If the patient is flooded with rewards, the learning paradigm is jeopardized. By increasing or decreasing the number of rewards needed to earn a score, the clinician can shape the EEG changes more easily. Auditory and visual reward modalities are used.

The patient is instructed in the reward system to be used during training. Training is relatively straightforward. The clinician sits beside the woman and verbally coaches her to achieve the reward. The patient is instructed to her eyes on the screen, to relax, to clear her mind, to focus her attention on the top of her head, and to try to have just one thought until an auditory or visual reward results. The instrumentation monitors the EEG data to determine whether the conditions for reward are being achieved, and rewards the patient accordingly.

The patient is seen three times per week, with each session lasting about 50 minutes.

| Week 1: PARAMETERS | |
| --- | --- |
| reward frequency: | 2–4 Hz |
| inhibit frequency: | 0–2 Hz |
| electrode sites: | CZ, PZ |

Session 1 is primarily used to establish training parameters, introduced the patient to biofeedback, and to give the patient a positive experience with biofeedback training. Sessions 2 and 3 carry on with the selected training parameters. Since each individual's EEG is unique, the initial session involves some routine experimentation to establish the proper training parameters. The parameters are adjusted as the patient meets training criteria. The patient meets her first training goals in sessions 2 and 3.

The patient does not report significant symptom change, but does report a "tingling sensation" in the head during sessions 2 and 3. The patient left the office saying, "I feel more awake," but reports that this feeling of being more awake lasted only a short time following the end of the session.

| Weeks 2-5: PARAMETERS | |
|---|---|
| reward frequency: | 4-5 Hz |
| inhibit frequency: | 0-2 Hz |
| electrode sites: | CZ, PZ for thirty minutes |
| | FZ, PZ for thirty minutes |

The patient's delta EEG activity is now being broadened into the theta band. During this training period, the patient reports falling asleep within 15 minutes of going to bed, reports that she is considering reducing her sleep medication, reports less "lower leg pain and burning in my feet", reports that she is able to remember a new telephone number long enough to write it down, and reports "feeling a bit more chipper."

| Weeks 6-12: PARAMETERS | |
|---|---|
| reward frequency: | 8-12 Hz |
| inhibit frequency: | 4-8 Hz |
| electrode sites: | CZ, PZ for 15 minutes |
| | FZ, PZ for 15 minutes |
| | CZ, C3 for 15 minutes |

During this training period, the patient reports sleeping without sleep medication, that leg pain does not begin until late in the day and does not reach original intensity, that she is answering the phone for her husband's private office, taking messages, and making appointments for her husband, that she is playing chess and reading a novel, and that her husband commented, "I feel like I have my wife back". Week 12 is the mid-treatment point in the training.

| Weeks 13-24: PARAMETERS | |
|---|---|
| reward frequency | 12-16 Hz |
| inhibit frequency: | 4-8 Hz |
| electrode sites: | CZ, PZ for 20 minutes |
| | FZ, PZ for 20 minutes |
| | CZ, C3 for 20 minutes |

These weeks constitute the final phase of treatment for increased normalization of EEG and stabilization of EEG changes. The patient's lower range delta activity is being further diminished, and theta activity is being further enhanced.

The patient reports stabilization of the prior improvements, but complains of increased frequency (not intensity) of leg pain, which may result from ceasing to use a cane to assist walking during week 14. She reports that sleep continues to occur within 15 minutes of going to bed, that memory continues to improve, increased receptionist duties at her husband's office, more interest and self-confidence to partake in conversations, and that she feels her responses are more appropriate to the conversation material. The patient states that she does not feel cured, but that quality of life has improved greatly.

Figure 4:
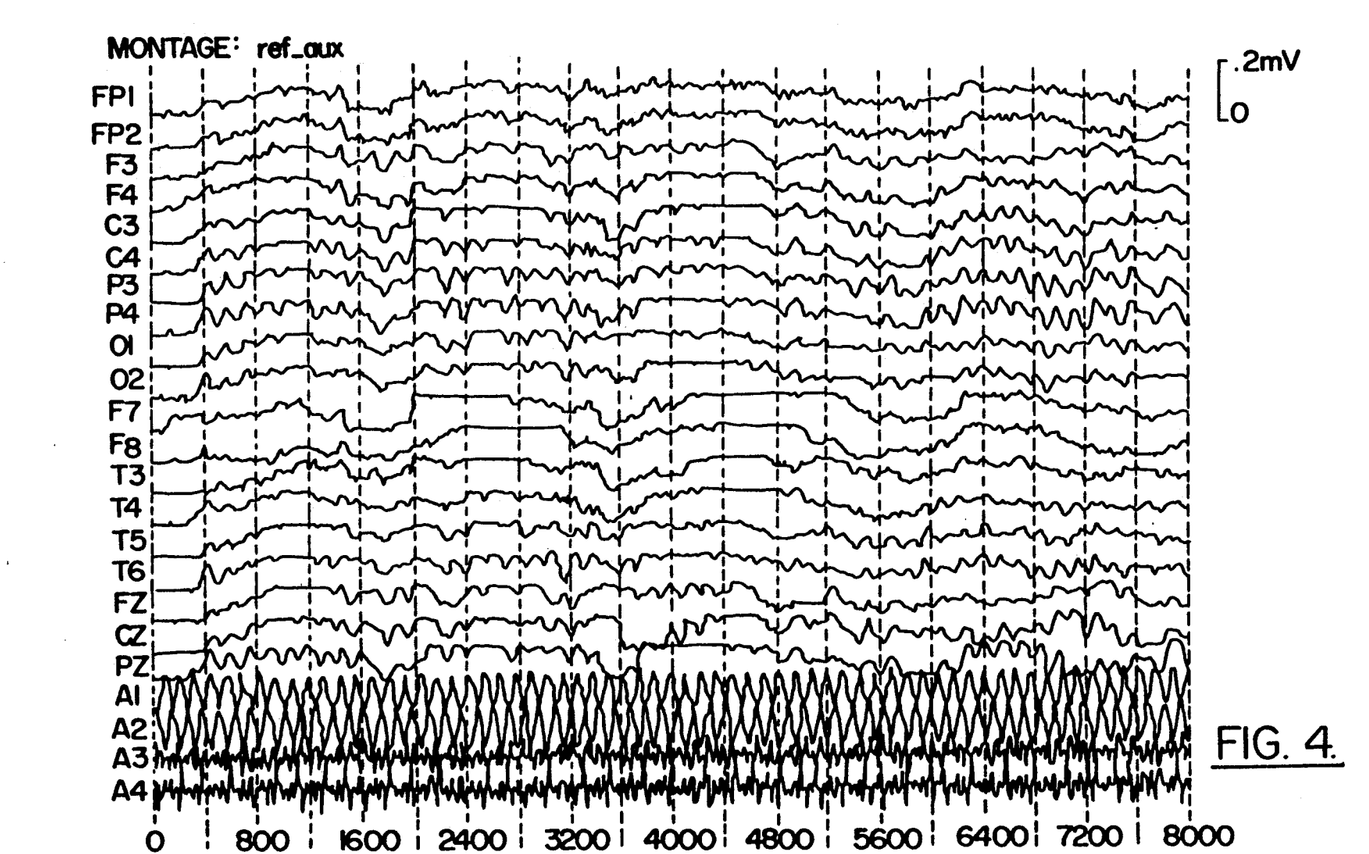
FIGS. 4 and 5 show changes in the EEG activity of a patient in response to training using the biofeedback-based method of the present invention.

Prior to the first session, the brain waves of the patient are evaluated to determine the brain areas where EEG dysfunction in the form of substantial delta or theta wave activity, may be first found. The Neurosearch-24 system is used. The protocol of the diagnostic method of the present invention including use of cognitive challenge, is followed. The results are set forth in Table 3 using a Percent Power format, and are based on 116 epochs. FIG. 4 shows the raw EEG data for epochs 83-84 (digits backwards). The data show dominant delta activity.

Figure 5:
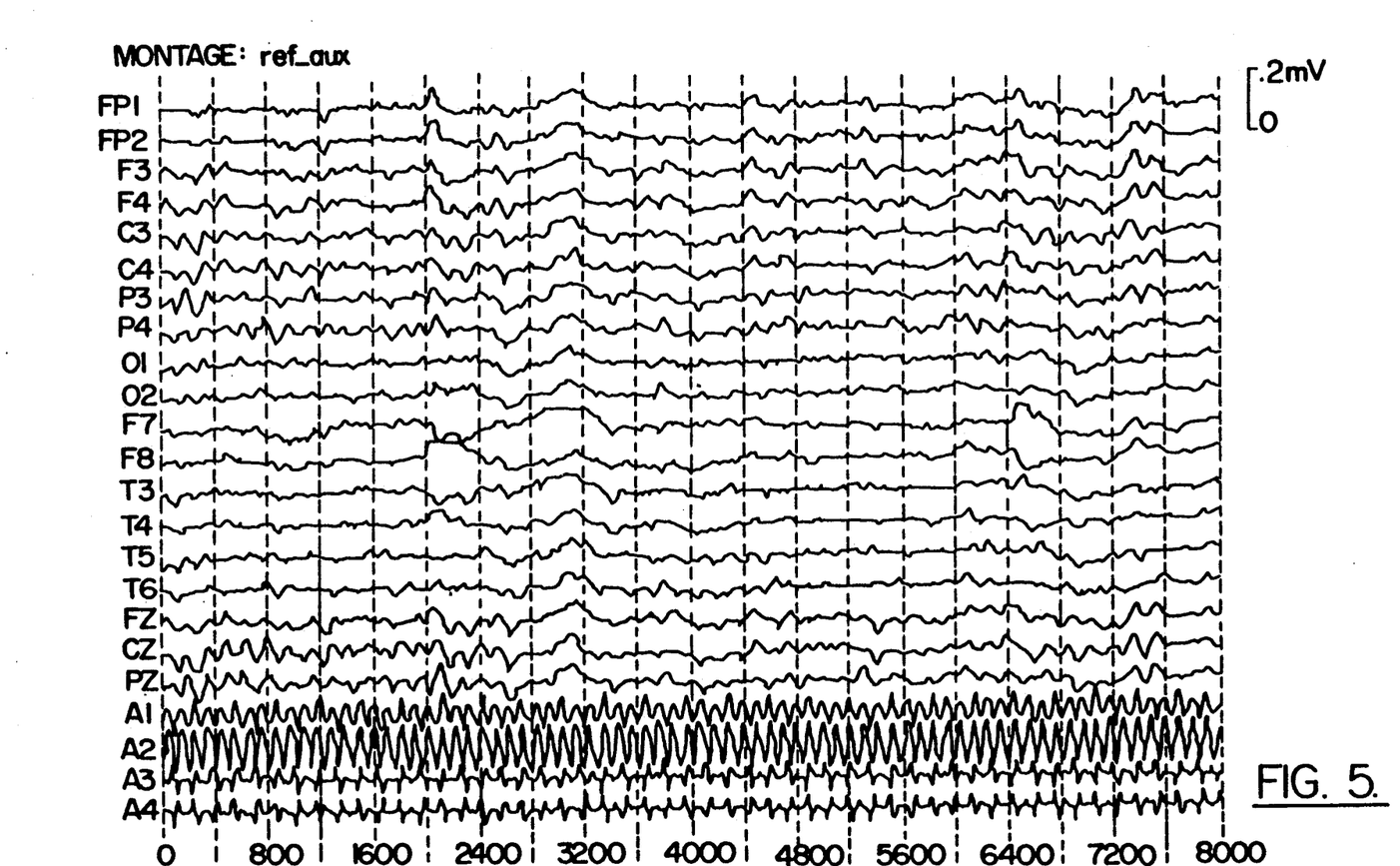

A day after the third session of week 12 (mid-treatment point), and a day after the final session of week 24, the patient's brain waves are again evaluated using the Neurosearch-24 system. The earlier-mentioned protocol is again followed. The mid-treatment results are set forth in Table 4 using a Percent Power format, and are based on 122 epochs (number of rejected epochs, 71). The post-treatment results are set forth in Table 5 using a Percent Power format, and are based on 110 epochs (number of rejected epochs, 102). FIG. 5 shows the raw EEG data for epochs 95-96 (digits backwards, post-treatment), and compared to FIG. 4 (digits backwards, pre-treatment), shows decreased amplitude of slow wave activity and decreased frequency of phase reversal.

Comparison of the data of Table 3 (pre-treatment) and Table 4 (mid-treatment) shows noticeable reduction in activity in the 0-2 Hz portion of the delta wave band, and increased theta band (4-8 Hz) activity. Comparison of the data of Table 4 and Table 5 (post-treatment) shows further significant reduction in activity in the 0-2 Hz range, and further increased activity in the theta wave band.

The present invention may be carried out with various modifications without departing from the spirit or the essential attributes thereof, and accordingly, reference should be made to the appended claims, rather than to the foregoing specification, as indicating the scope of the invention.

TABLE 3

| MEAN: | PERCENT POWER | | | | | | TOTAL |
| | 0-2 | 2-4 | 0-4 | 4-8 | 8-12 | 12-16 | (uV2) |
|---|---|---|---|---|---|---|---|
| F7 | 37.3% | 9.0% | 46.2% | 5.4% | 1.4% | 0.7% | 754.5 |
| F8 | 37.0% | 8.8% | 45.7% | 6.2% | 1.5% | 0.9% | 549.9 |
| T5 | 30.0% | 11.3% | 41.2% | 13.1% | 3.0% | 1.4% | 405.2 |
| FP1 | 35.1% | 9.8% | 44.9% | 7.0% | 1.9% | 1.2% | 647.2 |
| F3 | 30.5% | 11.9% | 42.5% | 11.8% | 2.3% | 0.9% | 563.5 |
| C3 | 29.7% | 10.6% | 40.3% | 16.0% | 2.6% | 0.9% | 534.3 |
| P3 | 27.0% | 11.0% | 38.0% | 20.4% | 2.6% | 1.1% | 497.0 |
| O1 | 28.2% | 12.3% | 40.5% | 15.0% | 2.8% | 1.3% | 450.3 |
| FZ | 30.0% | 11.7% | 41.8% | 13.5% | 2.3% | 0.7% | 545.1 |
| CZ | 28.2% | 11.2% | 39.4% | 17.9% | 2.6% | 0.8% | 631.7 |

TABLE 3-continued

| MEAN: | PERCENT POWER | | | | | | TOTAL (uV2) |
|---|---|---|---|---|---|---|---|
| | 0-2 | 2-4 | 0-4 | 4-8 | 8-12 | 12-16 | |
| PZ | 26.4% | 10.8% | 37.3% | 21.4% | 3.1% | 1.0% | 610.5 |
| FP2 | 35.9% | 9.1% | 45.1% | 6.5% | 1.9% | 1.5% | 649.9 |
| F4 | 30.1% | 11.3% | 41.5% | 13.7% | 2.4% | 1.0% | 527.4 |
| C4 | 28.5% | 10.5% | 38.9% | 18.4% | 2.8% | 0.9% | 482.4 |
| P4 | 26.6% | 11.4% | 38.0% | 20.2% | 2.9% | 1.0% | 509.9 |
| O2 | 29.3% | 11.7% | 40.9% | 14.0% | 2.7% | 1.4% | 420.2 |
| F8 | 37.0% | 8.8% | 45.7% | 6.2% | 1.5% | 0.9% | 549.9 |
| T4 | 33.0% | 10.4% | 43.4% | 9.6% | 2.4% | 1.2% | 363.3 |
| T6 | 28.5% | 12.0% | 40.5% | 15.0% | 2.8% | 1.2% | 410.1 |

TABLE 4

| MEAN: | PERCENT POWER | | | | | | TOTAL (uV2) |
|---|---|---|---|---|---|---|---|
| | 0-2 | 2-4 | 0-4 | 4-8 | 8-12 | 12-16 | |
| F7 | 28.4% | 13.2% | 41.7% | 12.5% | 2.9% | 1.3% | 211.0 |
| F8 | 30.4% | 11.4% | 41.8% | 12.4% | 2.7% | 1.3% | 202.3 |
| T5 | 29.3% | 11.3% | 40.6% | 13.1% | 3.6% | 2.1% | 286.5 |
| FP1 | 25.4% | 14.7% | 40.1% | 15.7% | 2.9% | 1.1% | 341.9 |
| F3 | 24.3% | 15.0% | 39.3% | 17.3% | 3.0% | 1.1% | 290.8 |
| C3 | 24.0% | 13.9% | 37.9% | 19.6% | 3.5% | 1.1% | 245.9 |
| P3 | 26.0% | 12.5% | 38.5% | 18.5% | 3.3% | 1.3% | 246.7 |
| O1 | 30.6% | 10.3% | 40.9% | 13.1% | 3.3% | 1.8% | 183.9 |
| FZ | 22.4% | 15.6% | 38.0% | 19.9% | 3.0% | 1.0% | 404.9 |
| CZ | 23.0% | 13.6% | 36.7% | 21.6% | 4.0% | 1.1% | 399.0 |
| PZ | 23.8% | 12.8% | 36.6% | 21.0% | 4.6% | 1.4% | 455.6 |
| FP2 | 25.4% | 14.6% | 40.0% | 15.9% | 2.9% | 1.1% | 311.9 |
| F4 | 24.4% | 14.8% | 39.2% | 17.6% | 3.0% | 1.0% | 295.7 |
| C4 | 26.8% | 12.2% | 39.0% | 17.4% | 3.4% | 1.2% | 213.3 |
| P4 | 27.9% | 11.4% | 39.3% | 16.6% | 3.5% | 1.3% | 208.1 |
| O2 | 29.4% | 11.4% | 40.9% | 13.7% | 3.2% | 1.4% | 179.8 |
| F8 | 30.4% | 11.4% | 41.8% | 12.4% | 2.7% | 1.3% | 202.3 |
| T4 | 31.5% | 10.6% | 42.1% | 11.6% | 2.8% | 1.3% | 229.9 |
| T6 | 29.5% | 9.9% | 39.3% | 13.2% | 4.9% | 3.3% | 226.1 |

TABLE 5

| MEAN: | PERCENT POWER | | | | | | TOTAL (uV2) |
|---|---|---|---|---|---|---|---|
| | 0-2 | 2-4 | 0-4 | 4-8 | 8-12 | 12-16 | |
| F7 | 27.7% | 14.3% | 42.1% | 12.8% | 2.4% | 0.8% | 222.3 |
| F8 | 27.8% | 12.9% | 40.7% | 15.3% | 2.3% | 1.1% | 293.3 |
| T5 | 21.1% | 15.4% | 36.5% | 20.1% | 4.7% | 2.2% | 150.3 |
| FP1 | 27.6% | 14.6% | 42.2% | 11.5% | 2.8% | 1.2% | 337.4 |
| F3 | 20.7% | 15.6% | 36.3% | 22.8% | 3.6% | 0.9% | 326.2 |
| C3 | 16.1% | 14.5% | 30.6% | 32.7% | 5.1% | 1.1% | 278.8 |
| P3 | 20.7% | 11.3% | 32.0% | 30.2% | 4.4% | 1.4% | 265.2 |
| O1 | 25.3% | 12.4% | 37.8% | 17.9% | 4.8% | 1.7% | 223.0 |
| FZ | 21.4% | 13.9% | 35.3% | 24.5% | 3.9% | 1.1% | 323.8 |
| CZ | 17.0% | 11.2% | 28.2% | 36.8% | 5.6% | 1.2% | 352.7 |
| PZ | 15.7% | 13.8% | 29.5% | 33.9% | 5.7% | 1.4% | 360.3 |
| FP2 | 28.2% | 14.1% | 42.3% | 11.4% | 2.5% | 1.5% | 356.7 |
| F4 | 21.8% | 13.3% | 35.1% | 24.7% | 3.9% | 1.2% | 316.6 |
| C4 | 17.8% | 12.9% | 30.7% | 32.7% | 4.5% | 1.4% | 259.1 |
| P4 | 15.2% | 15.3% | 30.4% | 31.8% | 5.8% | 1.5% | 250.3 |
| O2 | 23.6% | 13.7% | 37.3% | 18.5% | 5.2% | 1.7% | 185.1 |
| F8 | 27.8% | 12.9% | 40.7% | 15.3% | 2.3% | 1.1% | 293.3 |
| T4 | 22.7% | 13.6% | 36.3% | 21.0% | 4.8% | 1.5% | 111.3 |
| T6 | 14.0% | 18.1% | 32.1% | 27.6% | 6.3% | 1.8% | 168.8 |

I claim:

1. A neurodiagnostic method for chronic fatigue syndrome, said method comprising evaluating brain waves of an awake and alert patient presenting with symptoms of chronic fatigue syndrome, for predominance of slow wave activity in the range of from about 0 to 16 Hz, and confirming chronic fatigue syndrome on the basis of said symptoms and predominance of slow wave activity.

2. The method of claim 1, comprising selecting delta wave activity as the slow wave activity to provide the diagnostic confirmation.

3. The method of claim 1, comprising, prior to said evaluating, establishing a brain wave reading generally free of 60 Hz noise, and comprising, to assist said method, preparing a topographic brain map of the patient.

4. The method of claim 1, wherein in addition, slow wave activity in the 0 to 2 Hz range is dominant to wave activity in the 2 to 4 Hz range.

5. A neurodiagnostic method for chronic fatigue syndrome, said method comprising cognitively challenging a patient presenting with symptoms of chronic fatigue syndrome, and evaluating the patient's brain waves for increased slow wave activity, said method confirming chronic fatigue syndrome on the basis of increased slow wave activity under cognitive challenge.

6. The method of claim 5, wherein said slow wave activity is delta wave activity.

7. The method of claim 6, wherein said delta wave activity is in the range of about 2-4 Hz.

8. The method of claim 5, wherein said patient is challenged to repeat back a series of numbers in reverse order.

9. A neurodiagnostic method for chronic fatigue syndrome, said method comprising evaluating brain waves of a patient presenting with symptoms of chronic fatigue syndrome, for phase reversal in the delta wave band, and confirming chronic fatigue syndrome on the basis of phase reversal in the delta wave band.

10. The method of claim 9, further comprising cognitively challenging the patient during said evaluation, thereby confirming chronic fatigue syndrome on the basis of increased phase reversal under cognitive challenge.

11. The method of claim 9, further comprising preparing a topographic brain map of said patient, and evaluating said topographic brain map.

12. The method of claim 9, wherein said brain waves include brain waves emanating from the temporal lobes.

13. The method of claim 9, wherein said phase reversal is monitored in a wave frequency of no more than about two Hz.

14. A biofeedback-based treatment method for chronic fatigue syndrome, said method comprising setting suitable biofeedback instrumentation to indicate the combination of increased brain wave activity within a selected reward frequency and deceased brain wave activity within a selected inhibit frequency, monitoring the brian waves of a chronic fatigue syndrome patient for achievement of said combination, and indicating said achievement to the patient; wherein said selected inhibit frequency is initially in the range of approximately 0 to 8 Hz, and said selected reward frequency is greater than said selected inhibit frequency and is initially in the range of approximately 0 to 12 Hz; said method effecting increased brain wave activity within said selected reward frequency and decreased brain wave activity within said selected inhibit frequency.

15. The method of claim 14, wherein said selected inhibit frequency is in the range of approximately 0-2 Hz.

16. The method of claim 15, wherein said selected reward frequency is in the range of approximately 2-4 Hz.

17. The method of claim 15, wherein said selected reward frequency is in the range of approximately 4-8 Hz.

18. The method of claim 14, wherein said selected inhibit frequency is in the range of approximately 4-8 Hz.

19. The method of claim 18, wherein said selected reward frequency is in the range of approximately 8-12 Hz.

20. The method of claim 18, wherein said selected reward frequency is subsequently in the range of approximately 12-16 Hz.

21. The method of claim 14, further comprising prior to said monitoring step, selecting a sensory motor strip brain site for initial treatment.

22. The method of claim 14, further comprising prior to said monitoring step, determining the brain areas of EEG dysfunction and selecting a brain area of least dysfunction for initial treatment.

* * * * *